United States Patent
Langstrom et al.

(10) Patent No.: US 9,487,410 B2
(45) Date of Patent: Nov. 8, 2016

(54) PURIFICATION OF $^{68}$GE/$^{68}$GA GENERATOR ELUATE FROM FE(III) INTENDED TO IMPROVE SPECIFIC RADIOACTIVITY OF $^{68}$GA-BASED RADIOPHARMACEUTICALS

(75) Inventors: Bengt Langstrom, Uppsala (SE); Irina Velikyan, Uppsala (SE)

(73) Assignee: GE Healthcare Limited, Buckinghamshire (GB)

( * ) Notice: Subject to any disclaimer, the term of this patent is extended or adjusted under 35 U.S.C. 154(b) by 197 days.

(21) Appl. No.: 12/745,715

(22) PCT Filed: Dec. 1, 2008

(86) PCT No.: PCT/US2008/085095
§ 371 (c)(1),
(2), (4) Date: Jun. 2, 2010

(87) PCT Pub. No.: WO2009/102378
PCT Pub. Date: Aug. 20, 2009

(65) Prior Publication Data
US 2010/0275734 A1 Nov. 4, 2010

Related U.S. Application Data

(60) Provisional application No. 60/991,852, filed on Dec. 3, 2007.

(51) Int. Cl.
*C01G 15/00* (2006.01)

(52) U.S. Cl.
CPC ......... *C01G 15/003* (2013.01); *C01P 2006/80* (2013.01); *C01P 2006/88* (2013.01)

(58) Field of Classification Search
None
See application file for complete search history.

(56) References Cited

U.S. PATENT DOCUMENTS

2006/0022127 A1* 2/2006 Zyuzin ............... G21G 4/08
250/251

FOREIGN PATENT DOCUMENTS

| WO | 03/101972 | 12/2003 |
|---|---|---|
| WO | 2004/089517 | 10/2004 |
| WO | 2007/103233 | 9/2007 |

OTHER PUBLICATIONS

Aoyagi, "Separatoion of Gallium from other elements", Naagoya Kogyo Gijutsu Shikensho Hokokou, 1956, 5-1, 28-31.*
Velikyan, "Synthesis, Characterization and Application of 68Ga-labelled Peptides and Oligonucleotides" Thesis for the 'filosofie licentiate' degree Jan. 2004, Uppsala University (Velikyan'2004).*
Aoyagi, "Separation of Gallium from other elements", Naagoya Kogyo Gijutsu Shikensho Hokokou, 1956, 5-1, 28-31.*
Meyer et al, "68Ga-labelled DOTA-derivatised peptide ligands", E. J. of Nuclear Medicine and Molecular Imaging, 2004, 31, 1097-1104.*
Velikyan et al, "Microwave-Supported Preparation of 68Ga Bioconjugates with High Specific Radioactivity", Bioconjugate Chem. 2004, 15, 554-560.*
PCT/US2008/085095 ISRWO Dated Sept. 10, 2009.
Zhernosekov, et.al. "Processing of Generator-Produced 68GA for Medical Application" Journal of Nuclear Medicine, vol. 48, No. 10, 2007, p. 1741-1748.
Nagumo, Tadashi, et.al. "Manufacture of Gallium. IV. Anion Exchange Extraction of Gallium From Systems A1Cl—FeC13—GaCl3—HC1—H2O" Database CA [Online] Chemical Abstracts Service, Columbus, Ohio, Database Accession No. 60:58734.
Aoyagi "Separation of Gallium From Other Elements. V Concentration of a Trace of Gallium in Hydrochloric Acid Solution Containing a Large Amount of Other Elements by an Anion Exchange col. 2" Database CA [Online] Chemical Abstracts Service, Columbus, Ohio, Database Accession No. 55:117193.
Aoyagi "Separation of Galiium From Other Elements. II. Separation of Gallium From Iron by Anion-Exchange Resin in Hydrochloric Acid Solution" Database CA [Online] Chemical Abstracts Service, Columbus, Ohio, Database Accession No. 54:67297.

* cited by examiner

*Primary Examiner* — Melissa Swain
(74) *Attorney, Agent, or Firm* — Wood IP LLC

(57) ABSTRACT

The present invention provides a method of purifying $^{68}$Ge/$^{68}$Ga generator produced $^{68}$Ga from Fe (III). The invention further relates to an automated system within an existing Gallea Synthia prototype that provides purification $^{68}$Ga from various cations and preconcentrations of $^{68}$Ga. In general, the present invention further depicts the use of an automated system for the production of 68Ga-radiolabelled PET tracers with high specific radioactivity and a kit for purifying $^{68}$Ge/$^{68}$Ga generator produced $^{68}$Ga from Fe (III).

4 Claims, No Drawings

PURIFICATION OF $^{68}$GE/$^{68}$GA GENERATOR ELUATE FROM FE(III) INTENDED TO IMPROVE SPECIFIC RADIOACTIVITY OF $^{68}$GA-BASED RADIOPHARMACEUTICALS

This application is a filing under 35 U.S.C. 371 of international application number PCT/US2008/085095, filed Dec. 1, 2008, which claims priority to U.S. provisional application number 60/991,852 filed Dec. 3, 2007, the entire disclosure of which is hereby incorporated by reference.

FIELD OF THE INVENTION

The present invention relates to a method of purifying $^{68}$Ge/$^{68}$Ga generator produced $^{68}$Ga from Fe (III). The invention further relates to an automated system within an existing Gallea Synthia prototype that provides purification $^{68}$Ga from various cations and preconcentrations of $^{68}$Ga. The present invention further depicts the use of an automated system for the production of $^{68}$Ga-radiolabelled PET tracers with high specific radioactivity and a kit for purifying $^{68}$Ge/$^{68}$Ga generator produced $^{68}$Ga from Fe (III).

BACKGROUND OF THE INVENTION

Positron-emitting $^{68}$Ga ($T_{1/2}$=68 min) is of potential interest for clinical positron emission tomography (PET). It is a generator produced radionuclide, does not require cyclotron on site and thus easily available and relatively cheap. $^{68}$Ga is a suitable radiometal for PET radiopharmaceutical production. However, such obstacles as the chemical form of $^{68}$Ga after generator elution, the large elution volume and the contamination of other cations originating from the column material and $^{68}$Ge breakthrough may have limited its use. Methods to surmount some of these drawbacks have been developed[1,2] and might promote the wider use of $^{68}$Ga-based radiopharmaceuticals. Macrocyclic bifunctional chelators can form stable complexes with radiometal cations and covalently bind to macromolecules. The fact that the same chelator can complex different cations makes it possible to use the same biologically active molecule for diagnosis and therapy, employing corresponding radiometals. $^{68}$Ga has the potential for diagnosis, dosimetry, dose planning for chemo- and radiotherapy and follow up of response to chemo- and radiotherapy. These applications might require accurate quantification which is dependent on the specific radioactivity (SRA) of a tracer. This is especially important for the characterisation of high affinity binding sites, such as many peptide receptors. Another factor that necessitates the high SRA is the labelling of highly potent receptor agonists which can induce side effects. Cost of high molecular weight ligands might also be a factor to consider. A fast and reliable method for $^{68}$Ga-labelling of various macromolecules with high SRA has been developed.[1-3] However, we showed later that the achievement of SRA values comparable to the receptor concentration was most probably hindered by the presents of Fe(III). The latter is a strong competitor to $^{68}$Ga(III) in the complexation reaction with a chelator coupled to a peptide. The chemistry of Fe(III) and $^{68}$Ga(III) is very similar. Iron is an abundant cation and can be found in glassware, cartridges and chemicals. The removal of Fe(III) may improve the SRA and also omit any uncertainty over its role in the $^{68}$Ga-labelling process. The purification method[1,3] developed at Uppsala University/ Uppsala Imanet AB does not eliminate Fe(III). The method might be further improved by, for example, introduction of Fe(III) reduction to Fe(II). The adsorption profile of [FeCL$_4$]$^-$ is very similar to that of [$^{68}$GaCl$_4$]$^-$ from 0.1-6.0 M HCl. This makes it difficult to separate the two cations as the anion complex on the anion exchange resin. In contrast, Fe(II) is not adsorbed from 4.0 M HCl acid and would pass through the anion exchange resin without retention. The purification of the $^{68}$Ge/$^{68}$Ga generator eluate from Fe(III) might even further improve the SRA of $^{68}$Ga-based tracers comprising macromolecular ligands as well as small organic molecules. Specially, it could have a significant impact when using peptide, oligonucleotide, PNA, LNA, antibody, glycoprotein, protein and other biological macromolecule based ligands. Thus it might become possible to produce highly potent macromolecular $^{68}$Ga-based radiopharmaceuticals with high specific radioactivity and use them in humans without risk for pharmachological side effects. Moreover, $^{68}$Ga-based radiopharmaceuticals with high specific radioactivity would allow accurate quantification of PET examinations. This in turn would provide accurate in vivo quantification of receptor density for dosimetry, planning and follow up of chemo- and radiotherapy.

There is therefore a need in the art for a more effective and efficient method for purifying $^{68}$Ge/$^{68}$Ga generator produced $^{68}$Ga from Fe (III).

SUMMARY OF THE INVENTION

The present invention provides a method of purifying $^{68}$Ge/$^{68}$Ga generator produced $^{68}$Ga from Fe (III). The invention further relates to an automated system within an existing Gallea Synthia prototype that provides purification $^{68}$Ga from various cations and preconcentrations of $^{68}$Ga. The Gallea Synthia prototype is disclosed in patent publication number WO 02/102711. The present invention further depicts the use of an automated system for the production of $^{68}$Ga-radiolabelled PET tracers with high specific radioactivity and a kit for purifying $^{68}$Ge/$^{68}$Ga generator produced $^{68}$Ga from Fe (III).

One embodiment of the present invention depicts a method of purifying $^{68}$Ge/$^{68}$Ga generator produced $^{68}$Ga from Fe(III) wherein a high specific radioactivity of $^{68}$Ga-based radiopharmaceuticals, comprises of a bifunctional chelating agent and a vector selected from the group consisting of proteins, glycoproteins, lipoproteins, polypeptides, glycopolypeptides, lipopolypeptides, peptides, glycopeptides, lipopeptides, carbohydrates, nucleic acids, oligonucleotides, antibodies or a part, a fragment, a derivative or a complex of the aforesaid compounds and small organic molecules, is obtained.

The $^{68}$Ge/$^{68}$Ga generators are known in the art, see for instance C. Loc'h et al, J. Nucl. Med. 21, 1980, 171-173 or J. Schuhmacher et al. Int. J. appl. Radiat. Isotopes 32, 1981, 31-36. $^{68}$Ge may be obtained by cyclotron production by irradiation of, for instance Ga$_2$(SO$_4$)$_3$ with 20 MeV protons. It is also commercially available, e.g. as $^{68}$Ge in 0.5 M HCl. Generally, $^{68}$Ge is loaded onto a column consisting of organic resin or an inorganic metal oxide like tin dioxide, aluminium dioxide or titanium dioxide. $^{68}$Ga is eluted from the column with aqueous HCl yielding $^{68}$GaCl$_3$. Thus, $^{68}$Ga is in the form of $^{68}$Ga$^{3+}$, which could be used in the synthesis of $^{68}$Ga-radiolabelled complexes, e.g. for the production of $^{68}$Ga-radiolabelled PET tracers.

Suitable columns for $^{68}$Ge/$^{68}$Ga generators consist of inorganic oxides like aluminium dioxide, titanium dioxide or tin dioxide or organic resins like resins comprising phenolic hydroxyl groups (U.S. Pat. No. 4,264,468) or pyrogallol (J. Schuhmacher et al., Int. J. appl. Radiat. Isotopes 32, 1981, 31-36). In a preferred embodiment, a $^{68}$Ge/$^{68}$Ga generator comprising a column comprising titanium dioxide is used in the method according to the invention.

The concentration of the aqueous HCl used to elute $^{68}$Ga from the $^{68}$Ge/$^{68}$Ga generator column depends on the column material. Suitably 0.05 to 5 M HCl is used for the elution of $^{68}$Ga. In a preferred embodiment, the eluate is obtained from a $^{68}$Ge/$^{68}$Ga generator comprising a column comprising titanium dioxide and $^{68}$Ga is eluted using 0.05 to 0.1 M HCl, preferably about 0.1 M HCl.

DETAILED DESCRIPTION

Iron is an abundant cation and the chemistry of Fe(III) and $^{68}$Ga(III) is similar. Our study demonstrated that the Fe(III) was a strong competitor to $^{68}$Ga(III) in the complexation reaction with DOTA coupled to a peptide. DOTA is the chelator 1,4,7,10-tetraazacyclododecane-N,N',N'',N'''-tetraacetic acid. In addition, the $^{68}$Ga generator eluate was analyzed for the content of trace metals by inductively-coupled plasma atomic emission spectrometry (ICP-AES) using a Spectroflame P instrument (Spectro, Germany) and it was shown that the amount of Fe(III) exceeded that of $^{68}$Ga 200-2000 times dependent on the age of the generator and the amount of $^{68}$Ga available. Thus the purification of the generator eluate with regard to Fe(III) is the prior requirement for obtaining $^{68}$Ga radiopharmaceuticals with high specific radioactivity.

The adsorption profile of [FeCl$_4$]$^-$ is very similar as for [$^{68}$GaCl$_4$]$^-$ from 0.1-6.0 M HCl. This makes it impossible to separate these two cations on the anion exchange resin of the type we have been utilizing in our previous studies covered in the patents.[1,2] In contrast, Fe(II) is not adsorbed from 4.0 M HCl acid and thus goes through the anion exchange resin without retention.[4-6] Thus the reduction of Fe(III) to Fe(II) can be a possible means to purify the generator eluate from the Fe(III) and improve the specific radioactivity further. The reduction can be accomplished either in situ during the labeling step or prior to the labeling on the preconcentration/purification step. The former way might cause complications since the reductant should not affect the peptide stability or the $^{68}$Ga incorporation. Thus the selective reduction of the Fe(III) and elimination of Fe(II) prior to the labeling synthesis without perturbing the $^{68}$Ga (III) is more preferable. Below are several ways to accomplish the task. The solutions now considered will be adoptable to automation within the existing Gallea Synthia prototype.

One embodiment of the present invention depicts a method of purifying $^{68}$Ge/$^{68}$Ga generator produced $^{68}$Ga from Fe(III) wherein a high specific radioactivity of $^{68}$Ga-based radiopharmaceuticals, comprises of a bifunctional chelating agent and a vector selected from the group consisting of proteins, glycoproteins, lipoproteins, polypeptides, glycopolypeptides, lipopolypeptides, peptides, glycopeptides, lipopeptides, carbohydrates, nucleic acids, oligonucleotides, antibodies or a part, a fragment, a derivative or a complex of the aforesaid compounds and small organic molecules, is obtained.

The $^{68}$Ge/$^{68}$Ga generators are known in the art, see for instance C. Loc'h et al, J. Nucl. Med. 21, 1980, 171-173 or J. Schuhmacher et al. Int. J. appl. Radiat. Isotopes 32, 1981, 31-36. $^{68}$Ge may be obtained by cyclotron production by irradiation of, for instance Ga$_2$(SO$_4$)$_3$ with 20 MeV protons. It is also commercially available, e.g. as $^{68}$Ge in 0.5 M HCl. Generally, $^{68}$Ge is loaded onto a column consisting of organic resin or an inorganic metal oxide like tin dioxide, aluminium dioxide or titanium dioxide. $^{68}$Ga is eluted from the column with aqueous HCl yielding $^{68}$GaCl$_3$. Thus, $^{68}$Ga is in the form of $^{68}$Ga$^{3+}$, which could be used in the synthesis of $^{68}$Ga-radiolabelled complexes, e.g. for the production of $^{68}$Ga-radiolabelled PET tracers.

Suitable columns for $^{68}$Ge/$^{68}$Ga generators consist of inorganic oxides like aluminium dioxide, titanium dioxide or tin dioxide or organic resins like resins comprising phenolic hydroxyl groups (US-A 4,264,468) or pyrogallol (J. Schuhmacher et al., Int. J. appl. Radiat. Isotopes 32, 1981, 31-36). In a preferred embodiment, a $^{68}$Ge/$^{68}$Ga generator comprising a column comprising titanium dioxide is used in the method according to the invention.

The concentration of the aqueous HCl used to elute $^{68}$Ga from the $^{68}$Ge/$^{68}$Ga generator column depends on the column material. Suitably 0.05 to 5 M HCl is used for the elution of $^{68}$Ga. In a preferred embodiment, the eluate is obtained from a $^{68}$Ge/$^{68}$Ga generator comprising a column comprising titanium dioxide and $^{68}$Ga is eluted using 0.05 to 0.1 M HCl, preferably about 0.1 M HCl.

Yet another embodiment of the present invention shows a highly potent macromolecular $^{68}$Ga-based radiopharmaceuticals that have high specific radioactivity that are produced from a $^{68}$Ge/$^{68}$Ga generator thus allowing the use in humans without pharmacological side effects.

Still another embodiment of the present invention shows a method of obtaining $^{68}$Ga-based radiopharmaceuticals that have high specific radioactivity are produced from a $^{68}$Ge/$^{68}$Ga generator thus allowing accurate quantification of PET examinations.

Another embodiment of the present invention shows a method wherein $^{68}$Ga-based radiopharmaceuticals with high specific radioactivity are produced from a $^{68}$Ge/$^{68}$Ga generator thus allowing accurate in vivo quantification of receptor density for dosimetry, planning and follow up of chemo- and radiotherapy.

Still another embodiment of the present invention shows an automated system within an existing Gallea Synthia prototype for providing purification of $^{68}$Ga from Fe(III), Al(III), In(III), Ti(III), Ti(IV), Ni(II), Cu(I), Cu(II), Ge(IV), Pb(II) cations and preconcentrations of $^{68}$Ga. Please see publication number WO 02/102711 for a description of the Gallea Synthia prototype system.

A further embodiment of the present invention shows the use of an automated system with the aid of a $^{68}$Ge/$^{68}$Ga generator or an automated system within an existing Gallea Synthia prototype for the production of $^{68}$Ga-radiolabelled PET tracers with high specific radioactivity.

Yet another embodiment shows a kit for purifying a $^{68}$Ge/$^{68}$Ga generator produced $^{68}$Ga from Fe (III) by an automated system with the aid of a $^{68}$Ge/$^{68}$Ga generator or an automated system within an existing Gallea Synthia prototype.

The Reduction of Fe(III) in Solution with Subsequent Preconcentration and Purification of $^{68}$Ga is as Follows:

The acidification (4 M HCl) of the generator eluate is conducted in the presence of reducing agents such as Sn(II), Cu, Zn, Al, Ti(III) or organic hydrazine.[7-9] Fe(III) is reduced to Fe(II) and does not behave as tetra-chloro anion and does not retain on the anion exchange column (Chromafix, Chromafix 30-PS-HCO$_3$, Macharey-Nagel, Germany). In particular, the ferric ions are reduced to ferrous ions and the stannous ion (Sn$^{2+}$) is converted to stannic ion (Sn$^{4+}$). In the overall reaction, the stannous ion is the reducing agent, and therefore the substance oxidized, while pertechnetate is the oxidizing agent and therefore the substance reduced.

$$Sn^{2+}+Fe^{3+}\rightarrow Sn^{4+}+Fe^{2+}$$

Then the eluate solution is passed through the Chromafix anion exchanger to retain [$^{68}$GaCl$_4$]$^-$ and let through Fe(II).

Other inorganic reducing agents that can be used are zinc, copper or aluminium. For example, in the case of copper the overall reaction is as follows:

$$Cu(s)+2Fe^{3+}(aq)\rightarrow Cu^{2+}(aq)+2Fe^{2+}(aq)$$

Then the eluate solution is passed through the Chromafix anion exchanger to retain [$^{68}$GaCl$_4$]$^-$ and let through Fe(II) as well as Cu(II).

Organic hydrazine is a convenient reductant because the by-products are typically nitrogen gas and water.

$$N_2H_4+Fe^{3+}\rightarrow N_2+H_2O+Fe^{2+}$$

Then the eluate solution is passed through the anion exchanger to retain [$^{68}$GaCl$_4$]$^-$ and let through Fe(II).

The Reduction of Fe(III) on Resins Bearing Redox Groups with Subsequent Preconcentration and Purification of $^{68}$Ga is as Follows:

Reduction of Fe(III) can be performed using resins bearing redox groups such as hydroquinone, pyrocatechin, pyrogallol, borohydride, cyanoborohydride, triphenylphosphine oxide or sulfur trioxide pyridine (FIG. 1)[10-20] Such redox polymers can be prepared from chloromethylated polymers and the low-molecular organic redox systems.

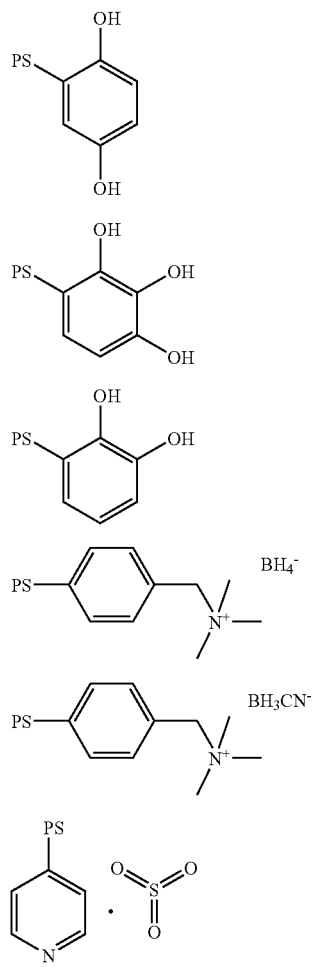

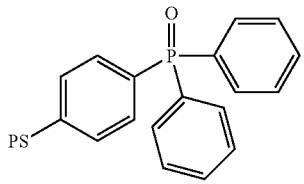

FIG. 1
1 - Hydroquinone; 2 - Pyrogallol;
3 - Pyrocatechol; 4 - Borohydride;
5 - Cyanoborohydride;
6 - Sulfur trioxide pyridine complex;
7 - Triphenylphosphine oxide.
PS stands for polymer support.

Phenolic substances are an important source of reductant capacity in aquatic solutions. For example, the oxidation of hydroquinone by Fe(III) is depicted in FIG. 2.

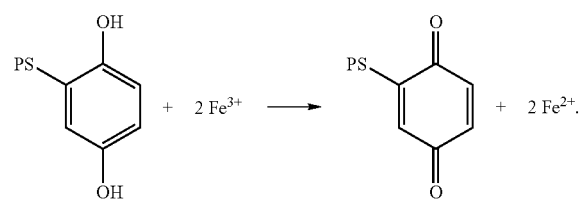

FIG. 2
Two Fe (III) are reduced and p-quinone produced.

Borohydrates supported on ion exchange resin are valuable reducing reagents as well (FIG. 3).

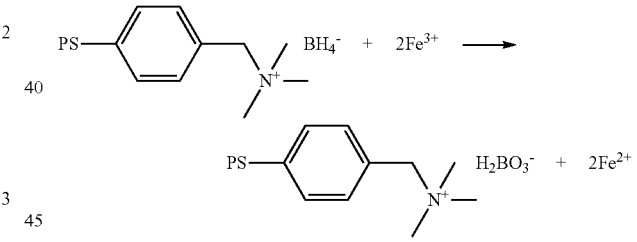

FIG. 3
Reduction of Fe(III) by borohydrate attached to polymer support Amberlyst IRA-400.

The use of functionalised resins is very convenient because of the easy work up and product purification. In addition it provides for recovery and regeneration of the supported reagent. Column packed with redox resin can be connected subsequently with the anion exchange column in order to preconcentrate and further purify $^{68}$Ga. The reduced Fe(II) is not adsorbed from 4.0 M HCl acid and thus goes through the Chromafix anion exchange resin without retention.

A Separation of $^{68}$Ga(III) from Fe(III) on Cationic and Anionic Exchange Resins is Presented as Follows:

Cationic and anionic exchange separation utilizing the difference in distribution coefficients for iron and gallium are considered as well.[21-27] Both organic (Dowex, Amberlite type) and inorganic (titanium tungstate) ion exchangers are packed on a column to simplify the purification. Various eluents are used for selective elution and purification. In addition Fe(III) is reduced to Fe(II) before loading on a cation exchange resin. For this purpose NaI is used as a reducing agent.[28] The consequent selective elution with respective eluents may separate $^{68}$Ga(III) from Fe(III).

$$FeCl_3 + NaI \rightarrow FeCl_2 + NaCl + I_2$$

Alternatively, a conventional ion exchanger can be loaded with an ion that can be oxidized by Fe(III). The cation and anion exchangers comprising such ions as Sn(II) and SO$_3$ could respectively be used. In this case, an emission of this extra ion in the solution (in both reduced and oxidized states) can be inevitable. But the next step of the purification of the anion exchange resin from 4 M HCl would clean the eluate from this extra cation.

A Purification of $^{68}$Ga from Fe(III) Using Electroactive Conductive Polymers is as Follows:

A very attractive possibility is electrochemically controlled binding of Fe(III) provided by electroactive, conductive polymers such as polypyrrole, polyaniline and their derivatives (FIG. 4).[29, 30] Thus, Fe(III) is selectively fixed by applying a specific potential value supplied by redox active polypyrrole resins while non-retained $^{68}$Ga(III) flows through the column. This is possible due to the fact that Fe(III) is easier reduced than $^{68}$Ga(III) with the respective standard reduction potential values of 0.77 and −0.56. A potentiostat/galvanostat is used in the electronic cell in order to control the potential of the working electrode at a constant level with respect to the reference electrode. The control of the pH of the solution is very important to keep the electroactivity of the polypyrrole resin and can be regulated by NaOH.

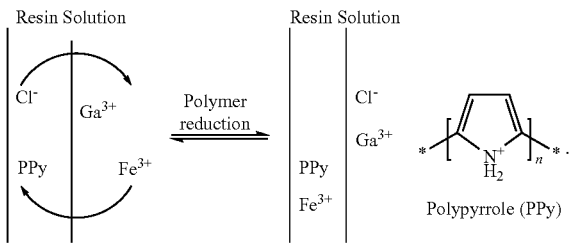

FIG. 4
Schematic depiction of the exchange of the cations during electrochemical redox process.

A Purification of $^{68}$Ga from Fe(III) by Precipitation and Subsequent Preconcentration of $^{68}$Ga is as Follows:

Separation of $^{68}$Ga(III) from Fe(III) can also be achieved by precipitation of iron trihydroxide from basic solution (pH>9.0) in which $^{68}$Ga(III) forms $^{68}$Ga(OH)$_4^-$ and stays in the solution.[31-33] The precipitation can be achieved by adding NaOH, KOH (1.5N) or NH4OH. Then a few drops of Al$_2$(SO$_4$)$_3$ is added to precipitate Fe$_2$O$_3$.

$$FeCl_3 + NaOH \rightarrow Fe(OH)_3 + NaCl$$

$$Fe(OH)_3 + Al_2(SO_4)_3 \rightarrow Fe_2O_3 + Al(OH)_3$$

Then the solution can be filtered and the filtrate used for the subsequent preconcentration of $^{68}$Ga on anion exchange column.

The proposed approaches (A-E) purify $^{68}$Ga from Fe(III). In addition, the subsequent use of the Chromafix anion exchange column provides the purification of $^{68}$Ga from Al(III), In(III), Ti(III), Ti(IV), Ni(II), Cu(I), Cu(II), Ge(IV), Pb(II) as well. The content of metal ions is assessed by inductively-coupled plasma atomic emission spectrometry (ICP-AES) using a Spectroflame P instrument (Spectro, Germany).

EXAMPLES

The invention is further described in the following examples which is in no way intended to limit the scope of the invention.

Examples

Experiemental Studies

A. Reduction of Fe(III) in Solution with Subsequent Preconcentration and Purification of $^{68}$Ga Example 1

Purification of $^{68}$Ga (III) from Fe(III) Using Reduction of Fe(III) with Stannous Ion and the Subsequent Anion Exchange Separation The $^{68}$Ge/$^{68}$Ga-generator is eluted with 6 mL 0.1 M HCl solution and acidified with 5 mL of 30% HCl. Then SnCl$_2$ (solid) is added to reduce Fe(III) to Fe(II). Then the solution is passed through an anion exchange column (Chromafix 30-PS-HCO$_3$, Macharey-Nagel (Germany)) at a flow rate of 4 mL/min (linear flow speed 25 cm/min) at room temperature. In HCl solution gallium forms strong anionic complexes with Cl$^-$ and the corresponding [$^{68}$GaCl$_6$]$^{3-}$ and [$^{68}$GaCl$_4$]$^-$ complexes are strongly adsorbed on the mentioned anion exchange resin from HCl concentrations >3 M, while Fe(II) passing through the resin without retention. Then $^{68}$Ga is eluted with small fractions of deionized water (50-200 µl) at a flow rate of 0.5 mL/min.

Example 2

Purification of $^{68}$Ga (III) from Fe(III) Using Reduction of Fe(III) with Solid Copper and the Subsequent Anion Exchange Separation The $^{68}$Ge/$^{68}$Ga-generator is eluted with 6 mL 0.1 M HCl solution and acidified with 5 mL of 30% HCl. Then Cu (solid) is added to reduce Fe(III) to Fe(II). Then the solution is passed through an anion exchange column (Chromafix 30-PS-HCO$_3$, Macharey-Nagel (Germany)) at a flow rate of 4 mL/min (linear flow speed 25 cm/min) at room temperature. In HCl solution gallium forms strong anionic complexes with Cl$^-$ and the corresponding [$^{68}$GaCl$_6$]$^{3-}$ and [$^{68}$GaCl$_4$]$^-$ complexes are strongly adsorbed on the Chromafix anion exchange resin from HCl concentrations>3 M, while Fe(II) passing through the resin without retention. Then $^{68}$Ga is eluted with small fractions of deionized water (50-200 µl) at a flow rate of 0.5 mL/min.

Example 3

Purification of $^{68}$Ga (III) from Fe(III) Using Reduction of Fe(III) with Hydrazine and the Subsequent Anion Exchange Separation The $^{68}$Ge/$^{68}$Ga-generator is eluted with 6 mL 0.1 M HCl solution and acidified with 5 mL of 30% HCl. Then hydrazine is added to reduce Fe(III) to Fe(II). Then the solution is passed through an anion exchange column (Chromafix 30-PS-HCO$_3$, Macharey-Nagel (Germany)) at a flow rate of 4 mL/min (linear flow speed 25 cm/min) at room temperature. In HCl solution gallium forms strong anionic complexes with Cl$^-$ and the corresponding [$^{68}$GaCl$_6$]$^{3-}$ and [$^{68}$GaCl$_4$]$^-$ complexes are strongly adsorbed on the mentioned anion exchange resin from HCl concentrations>3 M, while Fe(II) passing through the resin without retention. Then $^{68}$Ga is eluted with small fractions of deionized water (50-200 µl) at a flow rate of 0.5 mL/min.

B. Reduction of Fe(III) on Resins Bearing Redox Groups with Subsequent Preconcentration and Purification of $^{68}$Ga

Example 4

Reduction of Fe(III) on a Column Packed with Borohydride Functionalized Resin and Subsequent Purification of $^{68}$Ga (III) from Fe(III) Using Anion Exchange Separation The borohydride functionalized resin (Amberlyst IRA-400) is suspended in deionized water and loaded on a small plastic column. The latter is plugged with glass wool or polyethylene filter elements before packing with the wet resin. The $^{68}$Ge/$^{68}$Ga-generator is eluted with 6 mL 0.1 M HCl solution and the eluate is loaded on the column. After 10 minute incubation, the analytes are eluted with strong HCl acid and passed though the subsequently connected anion exchange column (Chromafix 30-PS-HCO$_3$, Macharey-Nagel (Germany)) at a flow rate of 4 mL/min (linear flow speed 25 cm/min) at room temperature. In HCl solution gallium forms strong anionic complexes with Cl$^-$ and the corresponding [$^{68}$GaCl$_6$]$^{3-}$ and [$^{68}$GaCl$_4$]$^-$ complexes are strongly adsorbed on the mentioned anion exchange resin from HCl concentrations>3 M, while Fe(III) reduced to Fe(II) passing through the resin without retention. Thereafter $^{68}$Ga is eluted with small fractions of deionized water (50-200 µl) at a flow rate of 0.5 mL/min.

Example 5

Purification of $^{68}$Ga (III) from Fe(III) Using Redox Active Hydroquinone Functionalized Polyacrylic Acid Polymer The $^{68}$Ge/$^{68}$Ga-generator is eluted with 6 mL 0.1 M HCl solution and loaded on a column packed with hydroquinone-bearing polyacrylic acid polymer. After 10 minute incubation, the analytes are eluted with strong HCl acid and passed though the subsequently connected anion exchange column (Chromafix 30-PS-HCO$_3$, Macharey-Nagel (Germany)) at a flow rate of 4 mL/min (linear flow speed 25 cm/min) at room temperature. In HCl solution gallium forms strong anionic complexes with Cl$^-$ and the corresponding [$^{68}$GaCl$_6$]$^{3-}$ and [$^{68}$GaCl$_4$]$^-$ complexes are strongly adsorbed on the mentioned anion exchange resin from HCl concentrations>3 M, while Fe(III) reduced to Fe(II) passing through the resin without retention. Thereafter $^{68}$Ga is eluted with small fractions of deionized water (50-200 µl) at a flow rate of 0.5 mL/min.

Example 6

Purification of $^{68}$Ga (III) from Fe(III) Using Redox Active Hydroquinone Functionalized Divinylbenzene Polymer The $^{68}$Ge/$^{68}$Ga-generator is eluted with 6 mL 0.1 M HCl solution and loaded on a column packed with hydroquinone-bearing divinylbenzene polymer. After 10 minute incubation, the analytes are eluted with strong HCl acid and passed though the subsequently connected an anion exchange column (Chromafix 30-PS-HCO$_3$, Macharey-Nagel (Germany)) at a flow rate of 4 mL/min (linear flow speed 25 cm/min) at room temperature. In HCl solution gallium forms strong anionic complexes with Cl$^-$ and the corresponding [$^{68}$GaCl$_6$]$^{3-}$ and [$^{68}$GaCl$_4$]$^-$ complexes are strongly adsorbed on the mentioned anion exchange resin from HCl concentrations>3 M, while Fe(III) reduced to Fe(II) passing through the resin without retention. Thereafter, $^{68}$Ga is eluted with small fractions of deionized water (50-200 µl) at a flow rate of 0.5 mL/min.

C. Separation of $^{68}$Ga(III) from Fe(III) on Cationic and Anionic Exchange Resins

Example 7

Purification of $^{68}$Ga (III) from Fe(III) Using an Anion Exchange Separation

The $^{68}$Ge/$^{68}$Ga-generator is eluted with 6 mL 0.1 M HCl solution. 5 mL of 30% HCl is added to the 6 mL of the generator eluate giving finally a HCl concentration of 4.0 M. The resulting 11 mL solution in total is passed through an anion exchange column (Chromafix 30-PS-HCO$_3$, Macharey-Nagel (Germany)) at a flow rate of 4 mL/min (linear flow speed 25 cm/min) at room temperature. Then Fe(III) is eluted with 1 mL of NH$_4$Cl. Afterwards the $^{68}$Ga is eluted with small fractions of deionized water (50-200 µl) at a flow rate of 0.5 mL/min.

Example 8

Purification of $^{68}$Ga (III) from Fe(III) Using an Anion Exchange Separation of the Malonic Complexes The $^{68}$Ge/$^{68}$Ga-generator is eluted with 6 mL 0.1 M HCl solution and the eluate is mixed with malonic acids with pH adjusted to 4.3 and the solution is then sorbed on the Dowex-21K. First, Fe(III) is eluted with 1 mL of NH$_4$Cl. Afterwards the $^{68}$Ga is eluted with 1 M HCl at a flow rate of 0.5 mL/min.

Example 9

Purification of $^{68}$Ga (III) from Fe(III) Using an Anion Exchange Separation of the Thiocyanate Complexes The $^{68}$Ge/$^{68}$Ga-generator is eluted with 6 mL 0.1 M HCl solution and the eluate is then loaded on the Amberlite IRA-400 with SCN$^-$ as a counter ion to form thiocyanate complexes. First, Fe(III) is eluted with 1 mL of 0.1 M HCl. Afterwards the $^{68}$Ga is eluted with 5 mL 1 M HCl at a flow rate of 0.5 mL/min, acidified with 6 mL of 30% HCl and is passed through an anion exchange column (Chromafix 30-PS-HCO$_3$, Macharey-Nagel (Germany)) at a flow rate of 4 mL/min (linear flow speed 25 cm/min) at room temperature. Then $^{68}$Ga is eluted with small fractions of deionized water (50-200 μl) at a flow rate of 0.5 mL/min.

Example 10

Purification of $^{68}$Ga (III) from Fe(III) Using Reduction of Fe(III) to Fe(II) and a Cation Exchange Separation The cation exchange resin (Dowex 50W) is suspended in 1 M HCl for 1 h, washed several times with deionized water, suspended in 1 M NH$_3$ for 10 min, washed with water and resuspended in 1 M HCl. After this procedure the resin is centrifuged and kept under 5M HCl for the further use. Small plastic tubes are used as small columns. They are plugged with glass wool or polyethylene filter elements and packed with the wet resin. Just before use the packed columns are conditioned and activated washing successively with 5 M HCl, 1 M HCl, H$_2$O and again 5 M HCl. The $^{68}$Ge/$^{68}$Ga-generator is eluted with 6 mL 0.1 M HCl solution. To the eluate 1% of NaI is added in order to reduce Fe(III) to Fe(II). The solution is loaded on the column filled with cation exchange resin. The column is washed with 4M HCl acid and then $^{68}$Ga is eluted with small fractions of deionized water (50-200 μl) at a flow rate of 0.5 mL/min.

Example 11

Purification of $^{68}$Ga (III) from Fe(III) Using Reduction of Fe(III) to Fe(II) and a Cation Exchange Separation (Dowex-50)

The $^{68}$Ge/$^{68}$Ga-generator is eluted with 6 mL 0.1 M HCl solution. Then SnCl$_2$ (solid) is added to reduce Fe(III) to Fe(II). Then the solution is passed through a cation exchange column (Dowex-50) at a flow rate of 4 mL/min (linear flow speed 25 cm/min) at room temperature. Fe(II) went through while $^{68}$Ga(III) is retained. Afterwards, the column is washed with 0.1 M HCl and $^{68}$Ga is eluted with small fractions of 1 M HCl (50-200 μl) at a flow rate of 0.5 mL/min.

D. Purification of $^{68}$Ga from Fe(III) Using Electroactive Conductive Polymers

Example 12

Purification of $^{68}$Ga (III) from Fe(III) Using a Column Packed with Redox Active Polypyrrole Resins The $^{68}$Ge/$^{68}$Ga-generator is eluted with 6 mL 0.1 M HCl solution and the eluate is added to the bath containing polypyrrole conducting polymer coated on titanium dioxide or on a polyurethane core. Fe(III) is fixed on the polymer by adjusting the potential. After the fixation of Fe(III) is complete the pure $^{68}$Ga(III) is filtered, acidified with 6 mL of 30% HCl and passed through an anion exchange column (Chromafix 30-PS-HCO$_3$, Macharey-Nagel (Germany)) at a flow rate of 4 mL/min (linear flow speed 25 cm/min) at room temperature. Then $^{68}$Ga is eluted with small fractions of deionized water (50-200 μl) at a flow rate of 0.5 mL/min.

E. Purification of $^{68}$Ga from Fe(III) by Precipitation and Subsequent Purification and Preconcentration of $^{68}$Ga

Example 13

Purification of $^{68}$Ga (III) from Fe(III) Using Precipitation and the Subsequent Anion Exchange Separation The $^{68}$Ge/$^{68}$Ga-generator is eluted with 6 mL 0.1 M HCl solution. Then NaOH (solid) is added to precipitate Fe(III) hydroxide from the basic solution (pH>9.0) while keeping $^{68}$Ga(OH)$_4^-$ in the solution. Then a few drops of Al$_2$(SO$_4$)$_3$ are added to precipitate Fe$_2$O$_3$. Then the solution is filtered, acidified with 6 mL of 30% HCl and passed through an anion exchange column (Chromafix 30-PS-HCO$_3$, Macharey-Nagel (Germany)) at a flow rate of 4 mL/min (linear flow speed 25 cm/min) at room temperature. Then $^{68}$Ga is eluted with small fractions of deionized water (50-200 μl) at a flow rate of 0.5 mL/min.

Specific Embodiments, Citation of References

The present invention is not to be limited in scope by specific embodiments described herein. Indeed, various modifications of the inventions in addition to those described herein will become apparent to those skilled in the art from the foregoing description and accompanying figures. Such modifications are intended to fall within the scope of the appended claims.

Various publications and patent applications are cited herein, the disclosures of which are incorporated by reference in their entireties.

What is claimed is:

1. A method of purifying $^{68}$Ga from Fe(III) in a $^{68}$Ga generator eluate which comprises:
   (i) eluting a $^{68}$Ge/$^{68}$Ga generator column with 0.05-0.1 M aqueous hydrochloric acid to give an eluate containing $^{68}$Ga and Fe(III);
   (ii) treatment of the eluate solution from step (i) to:
      (a) reduce the Fe(III) therein to Fe(II);
      (b) acidify with 30% w/v hydrochloric acid to give [$^{68}$GaCl$_4$]$^-$ in the eluate solution;
   wherein step (a) is carried out in the presence of a reducing agent comprising hydrazine, and steps (a) and (b) may optionally be carried out concurrently;
   (iii) passing the reduced eluate solution from step (ii) through an anion exchange column comprising HCO$_3^-$ counterions, wherein the [$^{68}$GaCl$_4$]$^-$ is retained on the anion exchange column and the Fe(II) passes through the anion exchange column without retention; and
   (iv) passing deionized water through the anion exchange column from step (iii) to elute purified $^{68}$Ga, having Fe(II) and Fe(III) removed therefrom and wherein the purified $^{68}$Ga has a purity that is suitable for use in chemotherapy and radiotherapy.

2. The method of claim 1 where the reduction of step (ii) is carried out by acidification of the eluate solution with said HCl in the presence of said reducing agent.

3. The method according to claim 1, further comprising converting the purified $^{68}$Ga to a $^{68}$Ga-based radiopharmaceutical.

4. The method according to claim 3, wherein said method is performed on an automated system.

* * * * *